United States Patent
Fadnavis et al.

(10) Patent No.: US 7,198,941 B2
(45) Date of Patent: Apr. 3, 2007

(54) POROUS VESSEL BIOREACTOR

(75) Inventors: Nitin Wasantrao Fadnavis, Hyderabad (IN); Bankupalli Satyavathi, Hyderabad (IN); Gurrala Sheelu, Hyderabad (IN); Vasantha Madhuri Kallakunta, Hyderabad (IN); Trishool Namani, Hyderabad (IN)

(73) Assignee: Council of Scientific and Industrial Research, New Delhi (IN)

(*) Notice: Subject to any disclaimer, the term of this patent is extended or adjusted under 35 U.S.C. 154(b) by 575 days.

(21) Appl. No.: 10/310,495

(22) Filed: Dec. 5, 2002

(65) Prior Publication Data

US 2004/0110280 A1   Jun. 10, 2004

(51) Int. Cl.
*C12M 1/16*   (2006.01)
(52) U.S. Cl. .................... 435/299.1; 435/813; 210/617; 210/291
(58) Field of Classification Search ............. 435/299.1, 435/813; 210/291
See application file for complete search history.

(56) References Cited

U.S. PATENT DOCUMENTS 4,543,332 A * 9/1985 Jao et al. .................... 435/180
5,728,577 A * 3/1998 Kuriyama ................ 435/299.1
6,214,088 B1 * 4/2001 Karamanev et al. .......... 75/711

FOREIGN PATENT DOCUMENTS

| DE | 3818776 A1 | * | 12/1989 |
| DE | 4207819 A1 | * | 9/1993 |
| JP | 01215276 A | * | 8/1989 |
| JP | 01269481 A | * | 10/1989 |
| JP | 02042974 A | * | 2/1990 |
| JP | 06181748 A | | 7/1994 |

* cited by examiner

*Primary Examiner*—William H. Beisner
(74) *Attorney, Agent, or Firm*—Abelman, Frayne & Schwab

(57) ABSTRACT

The present invention provides a porous vessel bioreactor apparatus for use in reaction with immobilized enzymes and/or microbial cells, said apparatus consisting of a vertically elongated reaction vessel having at least one liquid reactant inlet; at least one product outlet on the vessel; at least one porous vessel completely submerged in the reactant, said porous vessel having pore size ranging from 5 mm to 0.2 microns and a vertical length less than a level of the reactants to be maintained in the vessel, and immobilized bio-catalyst particles comprising the enzymes and/or microbial cells placed inside the porous vessel such that the liquid reactant is in contact with the bio-catalyst in both radial and axial directions.

16 Claims, 3 Drawing Sheets

Porous vessel bioreactor with immobilized biocatalyst

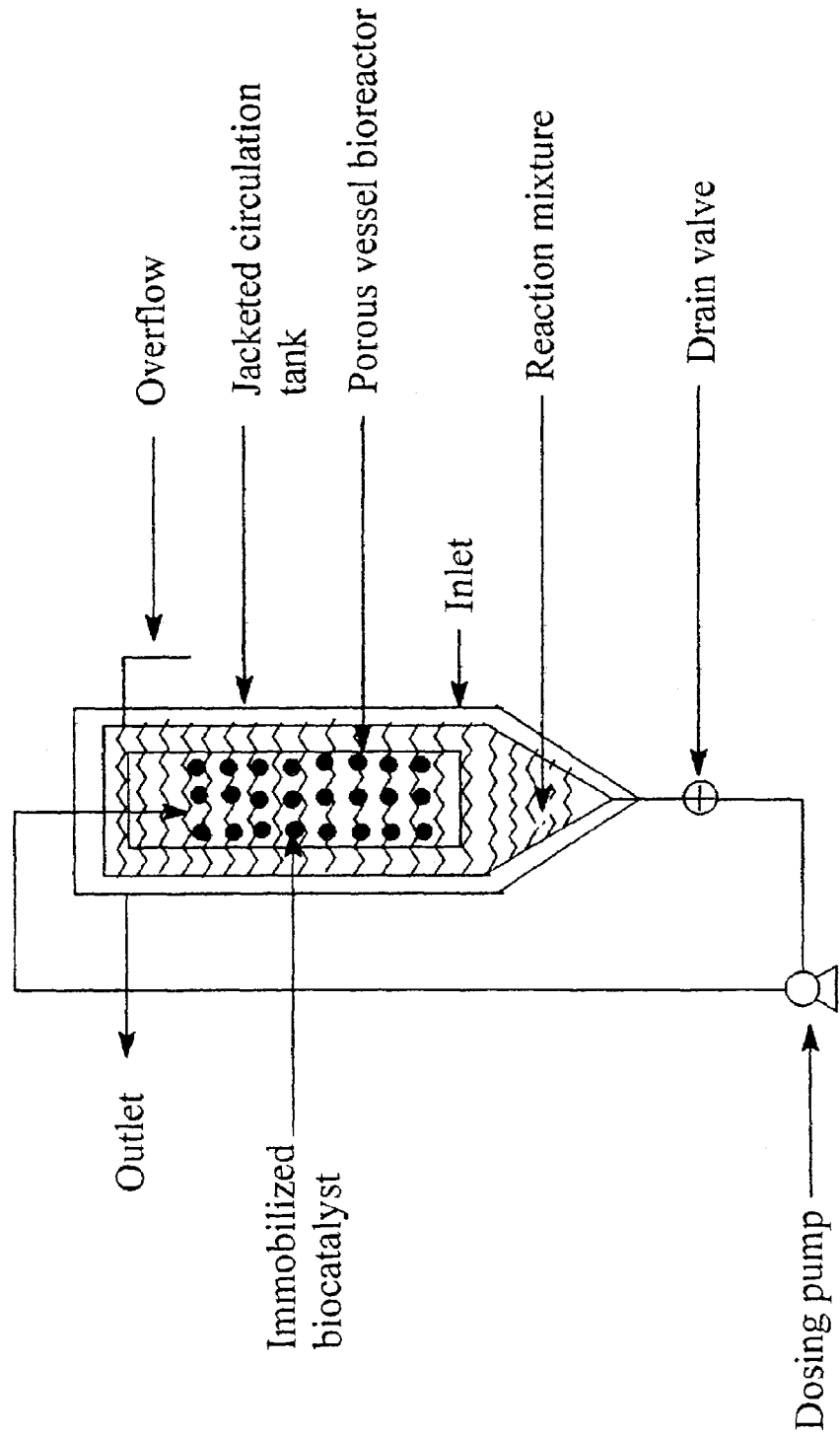
Figure 1 : Porous vessel bioreactor with immobilized biocatalyst

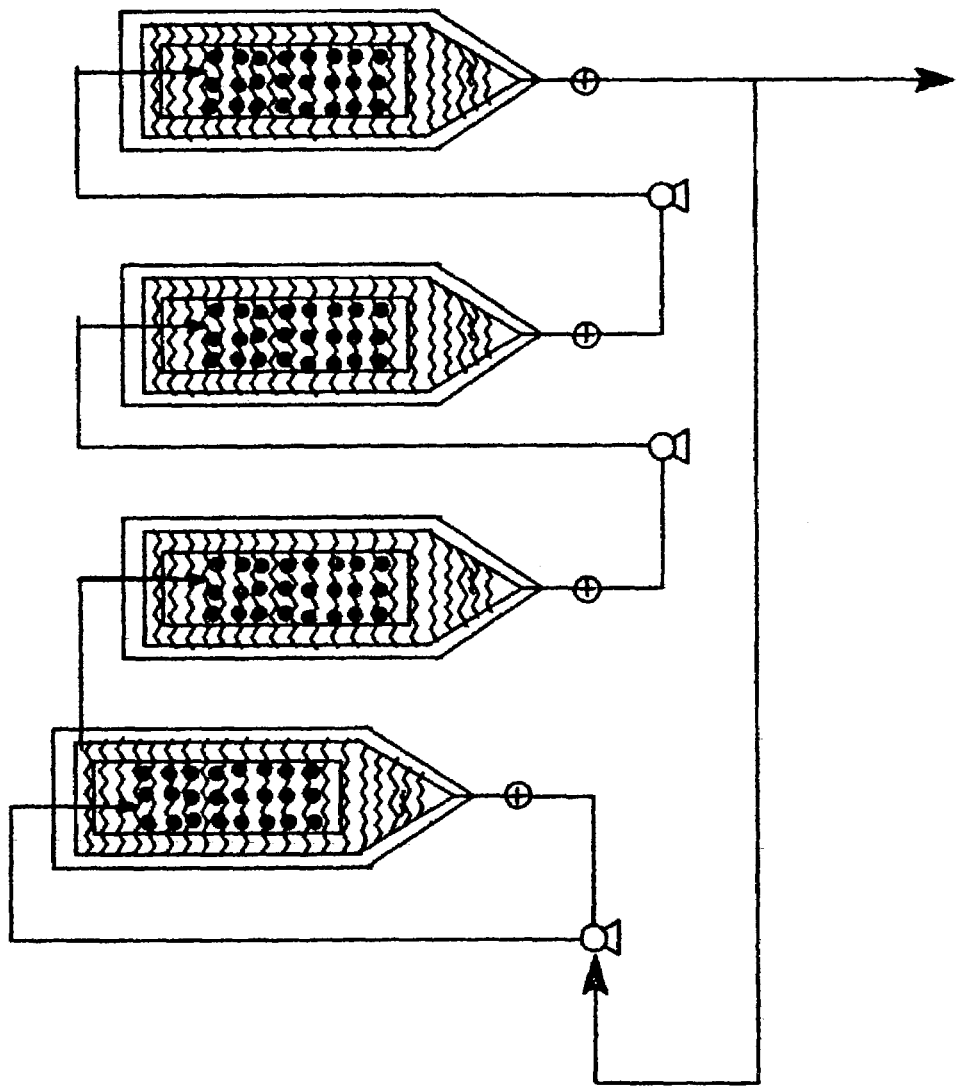
Figure 2: Porous vessel bioreactors in series

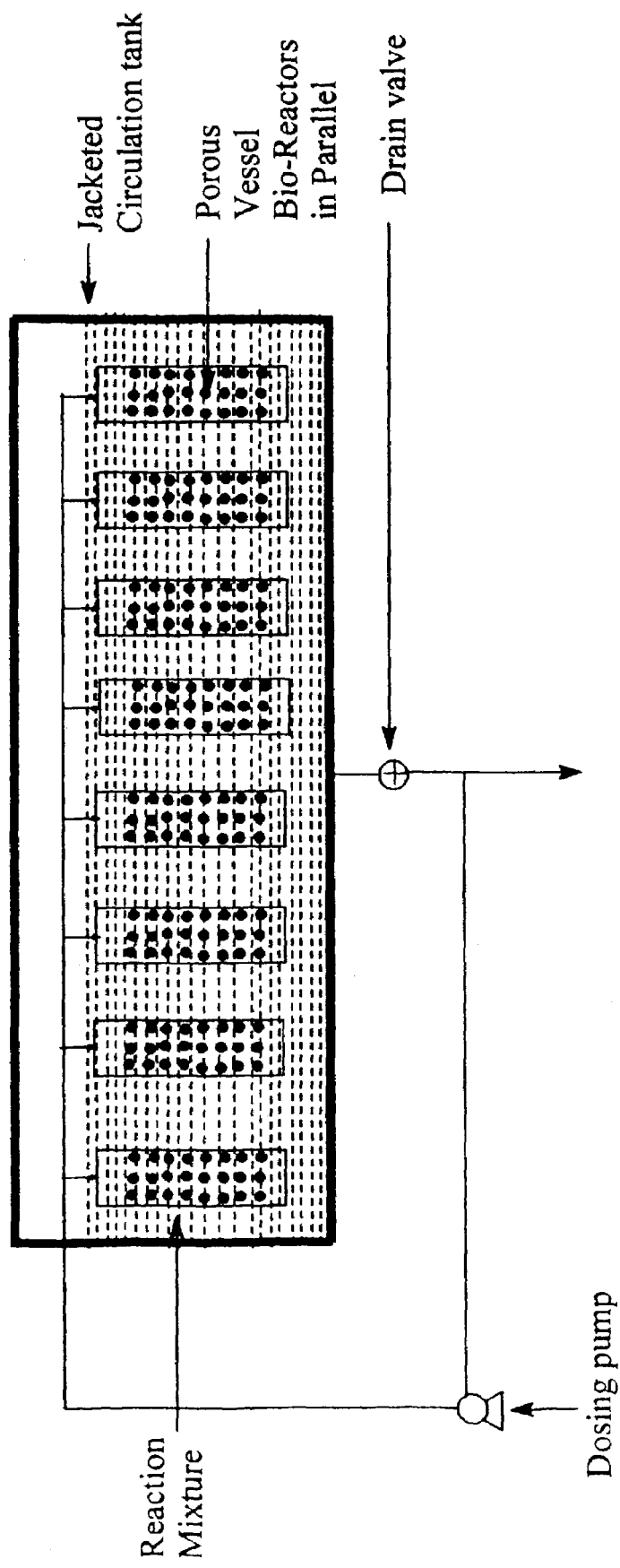
Figure 3 : Porous vessel bioreactors in parallel

POROUS VESSEL BIOREACTOR

FIELD OF THE INVENTION

The present invention relates to a novel porous vessel bioreactor apparatus for use in reactions with immobilized enzymes and/or microbial cells. The bioreactor apparatus broadly consists of a catalytic zone, which is inside a porous vessel submerged in a tank containing a circulating liquid. Immobilized enzymes and/or microbial cells that act as biocatalyst are placed inside the porous vessel and contact of the circulating liquid with the immobilized biocatalyst take place both in radial and axial directions. The feed point to the porous vessel can be located at any point along the dimensions of the porous vessel, preferably at either at a top or at a bottom end of the vessel. The present invention has the advantage of permitting greater contact between reactants and biocatalyst, which in turn increases the reaction rate and efficiency of the biocatalytic reaction. Another advantage of the present invention is that, the biocatalyst is separated from the reaction mixture simply by draining the circulating liquid.

BACKGROUND AND PRIOR ART TO THE INVENTION

Biochemical reactions involve biocatalysts (i.e. microorganisms, plant and animal cells, enzymes) and result in the transformation and production of biological and chemical substances. Vessels and apparatus (bioreactors) are required so that living organisms or enzymes can exhibit their activity (specific biochemical and microbial reactions) under defined conditions. In immobilized biocatalyst reactors, the biocatalysts may be immobilized in or on a carrier, immobilized by linkage among one another to form larger particles or confined within membrane barriers. Most of the reactors can be run in a batch, fed-batch or continuous mode.

Hitherto known equipments for using immobilized biocatalysts are the conventional reactors such as Continuous Stirred Tank Reactors (CSTR) and Packed Bed Reactors (PBR) as described in standard text books such as Ullmann's Encyclopedia Of Industrial Chemistry: Fifth edition, T. Campbell, R. Pfefferkom and J. F. Rounsaville Eds, VCH Publishers 1985, Vol A4, pp 141–170; Ullmann's Encyclopedia Of Industrial Chemistry: Fifth ed., B. Elvers, S. Hawkins and G. Schulz Eds, VCH Publishers, 1992, Vol B4, pp 381–433; J. B. Butt "Reaction Kinetics And Reactor Design" Prentice-Hall, Inc., 1980, pp 185–241.

The continuous stirred tank reactors consist of a tank containing a stirrer and, usually, fixed baffles to improve mixing. In a CSTR the immobilized enzyme is stirred with the substrate solution at fixed rpm and temperature. The reaction is monitored by appropriate technique and when the reaction is complete, the enzyme is separated from the reaction mixture by filtration and recycled. The CSTRs used for enzyme-catalyzed reactions assume a variety of configurations depending on the method employed to provide the necessary enzyme activity.

One of the popular ways of immobilization of an enzyme is to use an ultrafiltration membrane with pores sufficiently small to prevent the escape of the relatively large enzyme molecules in the solution However, the technique is useful only in cases of enzymes that have long term stability in solutions and are relatively inexpensive and hence, expendable.

Another technique is retention of immobilized enzymes in solution using a screen. A screen in the effluent line suffices if the enzyme is immobilized on insoluble particles, which are suspended in the reaction mixture as slurry. However, in such a system, the immobilized enzyme particles undergo attrition resulting in loss of enzyme as fines.

Yet another way of using immobilized enzyme in a stirred tank reactor is to employ pellets of immobilized enzyme held in a perforated container attached to an impeller. This configuration, which has also been widely used for the study of gas-phase reactions on supported metal catalysts, is intended to minimize mass-transfer resistance between the liquid phase and the immobilized-enzyme pellets. However, the size of the particle becomes very important in such cases and can lead to severe external mass transfer limitations.

Packed bed reactors are also used for biocatalytic processes. These reactors contain a settled bed of immobilized enzyme particles. The reaction mixture enters continuously from one end and the product moves out from the other end of the reactor. These reactors are like columns, and the degree of reaction, for a fixed flow rate, is proportional to the length of reactor column. A turbulent flow of reaction mixture through the column is preferred as it improves mixing. These reactors are preferred only in cases of processes involving product inhibition, substrate activation and reaction reversibility. However, colloids or precipitates formed during the reaction may clog up packed bed reactors. Also, temperature and pH are not easily regulated. Due to compact packing, excessive pressure drops are encountered which form the major bottleneck for the packed bed reactors. Channelling is also encountered which leads to improper contact between the biocatalyst and the reactants.

In the fluidtzed bed bioreactors the immobilized enzyme particles are fluidized, i.e., the particles become suspended in substrate stream, by the flow of the substrate stream. The immobilized enzyme particles are usually quite small, e.g., 20–40 μm in diameter, if their density is sufficiently high, otherwise larger particles have to be used to prevent them from being flown out of the reactor These reactors have kinetic properties between continuous flow stirred tank reactors and packed bed reactors. Fluidization of the bed requires a large power input, and such reactors are difficult to scale up. These reactors also need very high flow rates causing attrition of the biocatalyst and loss of the enzyme activity.

A membrane reactor uses a membrane, for e.g., a dialysis membrane, to contain the enzyme in a chamber into which the substrate moves and the product moves out. Each reactor contains hundreds of such fibres into which the enzyme is retained. The substrate is kept in the main chamber of the reactor. The substrate flow is adjusted to achieve the desired level of conversion. These reactors are easy to establish, permit the use of more than one enzyme to catalyze a chain of reactions, allow easy replacement of enzymes and are useful in producing small-scale (g to Kg) quantities. The chief limitations of these systems are: Regular replacement of membranes adds to cost and the need for substrate diffusion through the membrane often limits applications.

OBJECTS OF THE INVENTION

The main object of the present invention is to provide an improved porous vessel bioreactor apparatus for use in reactions with immobilized enzymes and/or microbial cells that obviates the drawbacks of the conventional reactors as detailed above.

Another object of the invention is to design a configuration that allows easy separation of the reactants from the biocatalyst.

Still another object of the present invention is to develop an improved porous vessel bioreactor apparatus which is simple to operate and easy for scale-up.

Yet another object of the present invention is to develop an improved porous vessel bioreactor apparatus wherein the materials used for construction does not react with the reactants or products and does not interfere with the native structure of the biocatalyst.

SUMMARY OF THE INVENTION

The present invention relates to a novel porous vessel bioreactor apparatus for use in reactions with immobilized enzymes and/or microbial cells. The bioreactor apparatus broadly consists of a catalytic zone, which is inside a porous vessel submerged in a tank containing a circulating liquid. Immobilized enzymes and/or microbial cells that act as biocatalyst are placed inside the porous vessel and contact of the circulating liquid with the immobilized biocatalyst take place both in radial and axial directions. The feed point to the porous vessel can be located at any point along the dimensions of the porous vessel, preferably at either at a top or at a bottom end of the vessel. The present invention has the advantage of permitting greater contact between reactants and biocatalyst, which in turn increases the reaction rate and efficiency of the biocatalytic reaction. Another advantage of the present invention is that, the biocatalyst is separated from the reaction mixture simply by draining the circulating liquid.

DETAILED DESCRIPTION OF THE INVENTION

Accordingly, the present invention provides a porous vessel bioreactor apparatus for use in reaction with immobilized enzymes and/or microbial cells, said apparatus consisting of a vertically elongated reaction vessel having at least one liquid reactant inlet; at least one product outlet on the vessel; at least one porous vessel completely submerged in the reactant, said porous vessel having pore size ranging from 5 mm to 0.2 microns and a vertical length less than a level of the reactants to be maintained in the vessel, and immobilized bio-catalyst particles comprising the enzymes and/or microbial cells placed inside the porous vessel such that the liquid reactant is in contact with the bio-catalyst in both radial and axial directions.

In an embodiment of the present invention, the reaction vessel further comprises a conical shaped bottom, a mechanism to maintain constant level of reactant in the reaction vessel and a means for re-circulating the reactant.

In another embodiment of the present invention, the mechanism to maintain constant level of reactant is a raised outlet raised to the level of the reactant in the reaction vessel.

In yet another embodiment of the present invention, the liquid reactant is re-circulated either manually or using a pumping means.

In still another embodiment of the present invention, the pumping means is selected from the group consisting of dosing pump and a metering pump.

In one more embodiment of the present invention, the reaction vessel further comprises a jacket and one or more heating coils to maintain isothermal conditions inside the reactor vessel.

In one another embodiment of the present invention, the reactant inlet terminates proximate to the porous vessel.

In a further embodiment of the present invention, the reactant inlet terminates inside the porous vessel such that the liquid reactant from the reactant inlet is in contact with the bio-catalyst in both radial and axial directions.

In an embodiment of the present invention, the product outlet is located at a bottom of the reaction vessel.

In another embodiment of the present invention, the porous vessel is constructed of clay based materials or metallic materials.

In yet another embodiment of the present invention, the clay based materials is selected from silica and porcelain.

In still another embodiment of the present invention, the metallic material is selected from the group consisting of stainless steel, brass, copper and aluminium.

In one more embodiment of the present invention, the immobilized bio-catalyst is immobilized enzyme or immobilized cell.

In one another embodiment of the present invention, the enzyme or the cell is immobilized on a solid support selected from the group consisting of copolymer of methylacrylamide, N,N'-methylene-bis(acrylamide) and monomer carrying oxirane group (Eupergit C), copolymer of acrylamide and N,N'methylene-bis(acrylamide), microemulsion based organo-gels containing glutaraldehyde cross-linked gelatin or gelatin-alginate composites crosslinked with glutaraldehyde to obtain the immobilized bio-catalyst.

In a further embodiment of the present invention of the present invention, the immobilized bio-catalyst is in the form of beads, flakes, granules, pellets or extrudes.

In an embodiment of the present invention, two or more porous vessels having the bio-catalyst are placed inside the reaction vessel.

In another embodiment of the present invention, the plurality of porous vessels are placed in parallel or in series inside the reaction vessel.

In yet another embodiment of the present invention, the porous vessel contains one or more immobilized enzymes or cells.

In still another embodiment of the present invention, a catalytic zone is formed inside the porous vessel.

In one more embodiment of the invention, the immobilized biocatalyst is contacted with a solution of the reactants by recirculating the liquid using a pump.

In one another embodiment of the invention, the immobilized btocatalyst is placed in one or more than one porous vessel in series, in a common circulating tank or several porous vessels in separate circulating tanks connected in parallel or in series.

In a further embodiment of the invention all the porous vessel bioreactors connected either in series or in parallel may contain the same biocatalyst or different btocatalysts.

In an embodiment of the invention the outlet from the circulating tank may be overflow or liquid can be drawn from the dram valve placed at the bottom of the circulating tank.

In another embodiment of the invention, the separation of the biocatalyst from the reaction mixture is done by draining the circulating liquid from the circulating tank.

BRIEF DESCRIPTION OF THE ACCOMPANYING DRAWINGS

In the drawings accompanying the specification,

FIG. 1 represents the porous vessel bioreactor with immobilized biocatalyst.

FIG. 2 represents the biorector having the porous vessels connected in series.

FIG. 3 represents the biorector having the porous vessels connected in parallel.

The invention is described in the following example by way of illustration only and should not be construed to limit the scope of the invention. The examples provided describe the use of porous vessel bioreactor for preparation of chiral intermediates using immobilized biocatalysts.

The Porous Vessel Bioreactor: The porous vessel bioreactor designed in accordance with the present invention consists of a stainless steel jacketed circulating tank of 150 mm diameter and 1500 mm length provided with a drain valve and an outlet as illustrated in FIG. 1. A porous vessel bioreactor also made of stainless steel having a nominal length of 1000 mm, diameter of 60 mm, 2.5 mm thickness and average pore size of 100 microns, is submerged in the circulating tank. The inlet to the porous vessel is placed on top as shown in the FIG. 1. The immobilized biocatalyst particles are placed inside the porous vessel as beads, flakes, granules, pellets, or extrudes. Provision is made for the outlet of the outer circulating tank in such a way that the liquid level is above the level of the catalyst bed. The outlet from the circulating tank is connected to inlet of a dosing pump of capacity ranging from 10 ml/min to 300 ml/min. The outlet from the pump is connected to the inlet of the porous vessel bioreactor. This type of reactor is most suitable than the conventional bioreactors since the flow of the liquid from the bioreactor is both radial and axial. This avoids fouling or blocking of the membrane pores and the pressure drop across the column is minimal.

A schematic representation of the complete set-up is given in FIG. 1 Other configurations for the apparatus are given in FIGS. 2 and 3. FIG. 2 represents a configuration wherein the porous vessels are connected in series to form the bioreactor apparatus. FIG. 3 represents the configuration wherein the porous vessels are connected in parallel to for the bioreactor apparatus.

EXAMPLE 1

Preparation of 2-acetamido-2-deoxy-1-hydroxy-β-D-glucose triacetate i) Immobilization of porcine pancreatic lipase in calcium alginate-gelatin composites: 5 g of sodium alginate and 3 g gelatin were added to 100 ml distilled water in a conical flask and the flask was kept undisturbed for 1 h to soak the materials properly and then sterilised for 15 min at 120° C. The hot solution was allowed to cool to room temperature with constant stirring with a magnetic bead. 1 g of porcine pancreatic lipase was then added and stirred for 15 min. 3 ml of 25% glutaraldehyde solution was added and the contents were stirred for additional 15 min. This slurry was then transferred to a dropping funnel with a plastic tip and allowed to fall into cold (5° C.) 1 lit of 2% $CaCl_2$ solution drop wise. The beads were left in $CaCl_2$ solution for 30 min. for hardening. The supernatant was decanted and the beads were then washed with distilled water and stored in refrigerator till further use. Approximately 400 beads with 3.5 mm average diameter were obtained.

ii) Enzymatic hydrolysis: The beads containing immobilized lipase as obtained above were placed in the reactor and the solution of 10 g of 2-acetamido-2-deoxy-β-D-glucose tetracetate in 250 ml of 0.1 M tris-HCl buffer of pH 7.5 containing 10% dimethyl sulfoxide was recycled using an assembly as described in FIG. 1 till all the starting material was hydrolyzed. After the reaction, the reactants were drained and extracted with ethyl acetate {3×50 ml). The product, 2-acetamido-2-deoxy-1-hydroxy-β-D-glucose tri- acetate, was recovered (8.5 g) as a sticky gum after removal of ethyl acetate by evaporation. $^1H$ NMR ($CDCl_3$): δ 6.22 (d, 1H, NHα, j=10 Hz), 5.77 (d, 1H, NHβ, j=8.6 Hz), 5.32 (t, 1H, H3α, j=9.4 Hz), 5.22 (d, 1H, H1 α, j=4 Hz), 5 13 (dt, 2H, j=9), 4.74 (d, 1H, H1β, j=8.4 Hz), 4.38–3.91(m, 4H), 3.77–3.68 (m, 1H), 2.10 (s, 3H, acetyl), 2.09 (s, 3H, acetyl), 2.02 (s, 3H, acetyl). 1.97 (s, 3H, acetyl). $^{13}C$ NMR ($CDCl_3$) 91.60, 71.30, 68.70, 67.45, 62.49, 52.58 ppm. $[α]^{23}_D$=+49.1 (c 1, $CHCl_3$).

EXAMPLE 2

Preparation of (S)-α-hydroxy-3-phenoxy-benzeneacetonttrile Using a Stainless Steel Porous Vessel Bioreactor The racemic ester, (R,S)-Cyano(3-phenoxyphenyl)methyl butyrate, (750 g) prepared by the method described in literature by Fadnavis and co-workers (Fadnavis, N. W.; Luke Babu, R.; Sheelu, G.; DeshpandeA *Tetrahedron Asymmetry* 2000, 11, 3303–3309) is dissolved in a mixture of hexane (11 lit) and n-butanol (700 ml). The enzyme lipase from *Candida rugosa* (EC 3.1.1.3, Type VII, Sigma, USA) was immobilized in gelatin matrix according to the procedure described in literature by Fadnavis and Koteshwar (Fadnavis, N. W. and Koteshwar, K. *Biotechnology Progress*, 1999, 15, 98–104). The enzyme powder of average particle size 1 mm (1.5 Kg powder, 250 g enzyme) was placed in the reactor and the reaction mixture of the racemic ester in hexane was circulated at a flow rate of 85 ml/min through the enzyme reactor. The reaction temperature was maintained at 25° C. by means of a constant temperature circulating water bath. The progress of the reaction was monitored by chiral HPLC as described in literature by Fadnavis and co-workers (Fadnavis, N. W.; Luke Babu, R.; Sheelu. G.; Deshpande. A. *J. Chromatography A* 2000, 189–193). The reaction was continued till almost all of the (R)-ester had reacted (8 h, 49% conversion) and the reaction came to a standstill. The reaction mixture was then drained from the bioreactor and the cycle was repeated The recovered reaction mixture consisting of unreacted (S)-ester, (R)-α-hydroxy-3-phenoxy-benzeneacetonitrile and butyl butyrate was then treated further to obtain (S)-α-hydroxy-3-phenoxy-benzeneacetonitrile as described in literature by Fadnavis and co-workers (Fadnavis, N. W.; Luke Babu, R.; Sheelu, G.; Deshpande, A. *Tetrahedron Asymmetry* 2001, 12, 1695–1699). The enzyme placed in the bioreactor was used over 50 cycles over a period of one month without loss of activity (<5%).

EXAMPLE 3

Resolution of N-phenylacetyl-2-amino-1-butanol with Immobilized Penicillin Acylase in a Ceramic Porous Vessel Bioreactor The bioreactor consisted of a ceramic porous vessel of porosity G-2 with diameter 35 mm and length 125 mm. This was placed in an outer double walled jacketed vessel with a drain valve. The enzyme Penicillin G Acylase (EC 3.5.1.11) immobilized on Eupergit C (70 g, enzyme activity 150 units/g; supplied by M/s Kopran Ltd, Mumbai, India) with mean particle diameter of 0.2 mm, was placed inside the porous vessel. The racemic N-phenylacetyl-2-amino-1-butanol was prepared as described in literature by Fadnavis and co-workers (Fadnavis, N. W.; Mohd Sharfuddin; Vadivel, S. K. *Tetrahedron Asymmetry* 1999, 10, 4495–4500). A solution of the racemic amide in water (206 g in 1 lit.), pH 7.0–8.0 was circulated through the porous vessel bioreactor by means of a dosing pump at a rate of 50 ml/min. The temperature of the bioreactor was maintained at 30° C. The reaction was followed by HPLC as described in the publication cited above. The reaction was stopped at 40% conversion stage (35 min.) and the reactants were drained for further work-up to obtain (S)-2-amino-1-butanol and (R)-N-phenylacetyl-2-amino-1-butanol as described in the publication cited above The enzyme was then used for next cycle. The enzyme was used for 200 cycles without loss of activity.

EXAMPLE 4

Reduction of Ethyl Benzoylacetate with Baker's Yeast Immobilized in Calcium Alginate Beads Using a Stainless Steel Porous Vessel Bioreactor Calcium alginate beads entrapping 200 g of baker's yeast (vol. 2.5 lit, average bead diameter 2 mm) prepared as described in literature by Bucke (Bucke. C. *Methods Enzymol.* 1987, 135, 175) were placed in the porous vessel bioreactor described in example 1. A solution of glucose (5 lit, 50 g/lit, in citrate buffer 0.02 M, pH 4.5) was circulated through the biocatalyst bed at a rate of 150 ml/min at 35° C. for 4 h to activate the beads. A solution of ethyl benzoyl acetate 10 g in 75 ml ethanol was added to the circulating liquid at a rate of 5 ml/h by means of a syringe pump. The reaction was continued for 24 h with maintenance of pH at 4.5 by intermittent addition of 10% ammonia solution. The reactants were then drained and extracted with chloroform to obtain ethyl (S)-3-hydroxy-3-phenyl propionate with e.e.>99% and 85% yield. $[\alpha]_D^{25}$ –41.8(c 1.3 $CHCl_3$).

Advantages of the Present Invention
1. Present invention overcomes the problems encountered during the use of conventional bioreactors. For example, the stirred tank reactors cause attrition of the biocatalyst resulting in loss of the catalytic activity. Also, the downstream processing after the reaction involves an extra unit operation of separation of the biocatalyst by filtration. The porous vessel bioreactor described in the present invention eliminates the step of filtration and overcomes the problem of enzyme loss through attrition and handling.
2. The porous vessel bioreactor described in the present invention is advantageous over the packed bed reactor since the flow of the liquid occurs in both radial as well as axial direction thereby overcoming the problems of pressure drops, channelling, disfigurement and compression effects.
3. The biocatalyst can be used in any of the immobilized forms such as beads, flakes, pellets, granules, and extrudes; and recycled several times, thus making the process economical.
4. The immobilized biocatalyst can be placed in one or more than one porous vessel in series, in a common circulating tank or several porous vessels in separate circulating tanks connected in parallel or in series making the scale-up easy.

What is claimed is:

1. A porous vessel bioreactor apparatus for use in reaction with immobilized enzymes and/or microbial cells, said apparatus comprising:
   a) a vertically elongated reaction vessel having at least one liquid reactant inlet and at least one product outlet on the vessel;
   b) said reaction vessel comprising a conical shaped bottom, a mechanism to maintain a constant level of reactant in the reaction vessel and a means for re-circulating the reactant;
   c) at least one porous vessel completely submerged in the reactant, said porous vessel having a pore size ranging from 5 mm to 0.2 microns and a vertical length less than the level of the reactants to be maintained in the vessel; and
   d) immobilized bio-catalyst particles comprising the enzymes and/or microbial cells placed inside the porous vessel such that the liquid reactant from the reactant inlet which terminates inside the porous vessel is in contact with the bio-catalyst in both radial and axial directions.

2. The apparatus of claim 1, wherein the mechanism to maintain a constant level of reactant is a raised outlet raised to the level of the reactant in the reaction vessel.

3. The apparatus of claim 1, wherein the means for re-circulating the liquid reactant is manual or a pumping means.

4. The apparatus of claim 3 wherein the pumping means is selected from the group consisting of dosing pump and a metering pump.

5. The apparatus of claim 1, wherein the reaction vessel further comprises a jacket and one or more heating coils to maintain isothermal conditions inside the reactor vessel.

6. The apparatus of claim 1, wherein the product outlet is located at a bottom of the reaction vessel.

7. The apparatus of claim 1, wherein the porous vessel is constructed of clay based materials or metallic materials.

8. The apparatus of claim 7, wherein the clay based materials is selected from silica and porcelain.

9. The apparatus of claim 7, wherein the metallic material is selected from the group consisting of stainless steel, brass, copper and aluminum.

10. The apparatus of claim 1, wherein the immobilized bio-catalyst is immobilized enzyme or immobilized cell.

11. The apparatus of claim 10, wherein the enzyme or the cell is immobilized on a solid support selected from the group consisting of copolymer of methylacrylamide, N,N'-methylene-bis(acrylamide) and monomer carrying oxirane group (Eupergit C), copolymer of acrylamide and N,N'methylene-bis(acrylamide), microemulsion based organo-gels containing glutaraldehyde cross-linked gelatin or gelatin-alginate composites crosslinked with glutaraldehyde to obtain the immobilized bio-catalyst.

12. The apparatus of claim 1, wherein the immobilized bio-catalyst is in the form of beads, flakes, granules, pellets or extrudes.

13. The apparatus of claim 1, wherein two or more porous vessels having the bio-catalyst are placed inside the reaction vessel.

14. The apparatus of claim 13, wherein the plurality of porous vessels are placed in parallel or in series inside the reaction vessel.

15. The apparatus of claim 1, wherein the porous vessel contains one or more immobilized enzymes or cells.

16. The apparatus of claim 1, wherein a catalytic zone is formed inside the porous vessel.

* * * * *